United States Patent [19]

Lau

[11] Patent Number: 5,422,284
[45] Date of Patent: Jun. 6, 1995

[54] METHOD OF PERFORMING AFFINITY SEPARATION USING IMMOBILIZED FLOCCULATING AGENT ON CHROMATOGRAPHIC SUPPORT

[75] Inventor: Hon-Peng P. Lau, Hockessin, Del.

[73] Assignee: E. I. Du Pont de Nemours and Company, Wilmington, Del.

[21] Appl. No.: 145,709

[22] Filed: Oct. 29, 1993

Related U.S. Application Data

[60] Division of Ser. No. 337,992, Apr. 14, 1989, Pat. No. 5,302,532, which is a continuation-in-part of Ser. No. 74,242, Jul. 16, 1987, abandoned.

[51] Int. Cl.⁶ ............... G01N 33/544; G01N 33/546; G01N 33/551; G01N 33/553
[52] U.S. Cl. .................. 436/528; 210/656; 210/661; 210/723; 210/807; 422/59; 436/524; 436/526; 436/531; 436/536; 436/538; 436/539; 436/541; 436/824; 530/412; 530/413; 530/418
[58] Field of Search ............ 210/656, 661, 723, 807; 422/59, 70; 436/524, 526, 528, 531, 536, 538, 539, 541, 824; 530/412, 413, 417, 418, 421

[56] References Cited

U.S. PATENT DOCUMENTS 4,661,408 4/1987 Lau et al. .................. 428/405
4,935,147 6/1990 Ullman et al. .............. 435/261

FOREIGN PATENT DOCUMENTS 2019378 10/1979 United Kingdom .

*Primary Examiner*—David Saunders
*Assistant Examiner*—Christopher L. Chin

[57] ABSTRACT

Disclosed is a primary chromatographic support containing an immobilized flocculating agent for use as a separation media for a secondary support consisting of microparticles used in affinity separation and heterogeneous immunoassays. In a specific embodiment, a flocculating agent such as polyethyleneimine is immobilized on a chromatographic resin packed in a column. The column so formed is then used to trap microparticles having an affinity ligand or binder for the ligand affixed thereon. Such microparticles are used as a solid support for the affinity reaction involved in a variety of immunoassay formats.

8 Claims, No Drawings

METHOD OF PERFORMING AFFINITY SEPARATION USING IMMOBILIZED FLOCCULATING AGENT ON CHROMATOGRAPHIC SUPPORT

CROSS REFERENCE TO RELATED APPLICATION

This application is a divisional of application Ser. No. 07/337,992 filed Apr. 14, 1989, now U.S. Pat. No. 5,302,532, issued Nov. 2, 1993, which is a continuation-in-part of application Ser. No. 07/074,242, filed Jul. 16, 1987, now abandoned.

TECHNICAL FIELD

This invention is related to chromatographic solid supports containing flocculating agent immobilized thereon for use in separation of microparticles and, more specifically, to chromatographic solid supports containing immobilized flocculating agent for use in affinity separation and heterogeneous immunoassay employing microparticles as solid support.

BACKGROUND ART

Separation of biomolecules is commonly achieved by means of affinity reaction employing the specific binding of a biomolecule with its binding partner immobilized on a solid support. Bioaffinity separation is defined as an affinity separation in which at least one of the components involved in the affinity reaction is biologically active or is of biological interest. Bioaffinity separations generally involve at least one biomacromolecule such as a protein or nucleic acid, as one of the components of the binding pair. Examples of such binding pairs include: antigen-antibody, substrate-enzyme, activator-enzyme, inhibitor-enzyme, complementary nucleic acid strands, binding proteins-vitamin, binding protein-nucleic acid, reactive dye-protein and others. The terms ligand and binder for the ligand will be used to represent the two components of a specific binding pair, the binder being complementary to the ligand of interest.

The most common means used to effect the separation of the bound material from that remaining unbound is to attach either a ligand or binder for the ligand to a solid support; then once the specific binding has occurred, to remove the solid from the liquid environment. This attachment to a solid support can be either covalent or noncovalent and can be either directly to the support or via a linker between the support and ligand or binder for the ligand.

Affinity separation is commonly a step in many multi-step processes. One example is the area of heterogeneous immunoassays. Here a bioaffinity separation is used to capture an analyte from a complex mixture, frequently, serum or plasma. After capturing the analyte, the contaminants are washed away and the analyte detected using any number of well-known assay protocols. Some solid supports used in heterogeneous immunoassays are ¼ inch plastic spheres, the inside of test tubes, the inside of microtiter plate wells, latex particles and magnetic particles.

Microparticles such as latex particles or magnetic particles are often preferred solid supports for use in affinity separation and heterogeneous immunoassay. Microparticles offer a high surface area providing enhanced coupling capacity for a ligand or binder for the ligand. In addition, microparticles remain substantially dispersed during a specific binding reaction allowing the immobilized ligand or binder for the ligand to be intimately mixed with the target binder for the ligand or ligand in the sample which shortens the reaction time. Since microparticles are substantially suspendible in solution, the slurry can be treated as a liquid reagent and delivered reproducibly and quantitatively which is an added advantage for easy handling of the solid support. However, separation of these particles is often tedious and labor intensive requiring centrifugation, filtration or a special magnetic separation device.

Despite the high magnetic field gradient requirement for separation, magnetic particles have been widely applied to heterogeneous immunoassays due to high surface area, efficiency of separation and ease of handling. Various types of magnetic particles suitable for use in immunoassay have been described by, for example, Hersh, et al., U.S. Pat. No. 3,933,997; Ithakissios, U.S. Pat. No. 4,115,534; Forrest, et al., U.S. Pat. No. 4,141,687; Mansfield, et al., U.S. Pat. No. 4,197,337; and Chagnon, et al., Danish Application DK 2,374,184.

The concept of using microparticles, particularly magnetic particles, to effect separation of bioactive materials as in immunoassays, has been extended over time to include affinity purification of enzyme, proteins or micro-organisms applicable to any adsorption-desorption process [Dunhill, P. et al., Biotech. Bioeng. (1974) 10, 987–990; Horisberger, M., Biotech. Bioeng. (1976) 18, 1647–1651]. In these applications, a simple and fast separation technique for the microparticles is also essential.

A flocculating agent is a substance which facilitates and accelerates aggregation of particulate matters from a suspension ultimately leading to precipitation of the aggregates in some situations. Flocculating agents are most commonly used in water purification for removal of both organic and inorganic particulate matters. Traditional flocculating agents include potassium sulfate, ferric chloride and ferric sulfate. More recently, polymeric flocculating agents have also been used for water purification applications. There are many other agents such as polyethyleneimine (PEI) or PRIMAFLOC ® flocculating reagent (Rohm and Hass, Philadelphia, Pa.) known in the art.

Hou, et al., U.S. Pat. No. 4,578,150, describes a filter device containing silica particles for the purposes of removing certain biological materials from a sample by adsorption. The silica particles are added simply to enhance the filtration efficiency. And a flocculating agent is added to improve the retention of the silica particles in the filter.

Chromatographic supports containing immobilized PEI have been described by Alpert, et al. in J. of Chromatography, Volume 185, 375–392, 1979; Vanecek, et al. in Analytical Chemistry, Volume 121, 156–159, 1982; and Flasher in EP Application 0,162,462. In all of these applications, PEI is used to provide ion-exchange properties for purification of proteins, particularly IgM class monoclonal antibodies, not as a flocculating agent.

While it is highly desirable to employ microparticles as solid support in affinity separation or heterogeneous immunoassay, inconvenient separation techniques of such particles have limited the utility, especially use on automated instruments. The method of this invention provides a simple, rapid and inexpensive means of separating microparticles using flocculating agent immobilized on chromatographic support.

SUMMARY OF THE INVENTION

The chromatographic support of this invention for use as a separation media for microparticles is comprised essentially of: (a) solid support and (b) flocculating immobilized agent thereon.

In another aspect of this invention, the chromatographic support for use in affinity separation and heterogeneous immunoassay is comprised essentially of: (a) primary solid support, (b) flocculating agent immobilized thereon, and (c) secondary support consisting of microparticles containing attached ligand or binder for the ligand flocculated onto the primary support of step (b).

The method of separating microparticles from a suspension containing said microparticles of this invention comprises the steps of:
a. forming a chromatographic support with a flocculating agent immobilized thereon; and
b. contacting the suspension of microparticles with said chromatographic support to trap the microparticles on the support.

Also included in this invention is the method of performing an affinity separation which comprises the steps of:
a. forming a primary chromatographic support with a flocculating agent immobilized thereon;
b. forming a secondary support consisting of microparticles containing attached ligand or binder for the ligand;
c. contacting the primary support of step a with the secondary support of step b to form an affinity support with said microparticles flocculated onto said primary support; and
d. contacting a sample suspected of containing a binder for the ligand or ligand complementary to the ligand or binder for the ligand attached on the affinity support of step c to separate said binder for the ligand or ligand from the sample.

Alternatively, the method of performing an affinity separation comprises the steps of:
a. forming a primary chromatographic support with a flocculating agent immobilized thereon;
b. forming a secondary support consisting of microparticles containing attached ligand or binder for the ligand;
c. contacting a sample suspected of containing a binder for the ligand or ligand complementary to the ligand or binder for the ligand attached on the microparticles of step b with said microparticles to capture the binder for the ligand or ligand from the sample onto the microparticles; and
d. contacting the reaction mixture of step c with the primary support of step a to trap the microparticles.

Yet in another aspect of this invention, the method of performing sandwich immunoassay for detection of a target antigen in a sample comprises the steps of:
a. forming a primary chromatographic support with a flocculating agent immobilized thereon;
b. forming a secondary support consisting of microparticles having a first antibody to the target antigen affixed thereon;
c. forming a ternary complex consisting of first antibody-antigen-second antibody by contacting the sample with said microparticles of step b and the second antibody to the target antigen coupled to a label;
d. contacting the reaction mixture of step c with the support of step a to trap microparticles containing the ternary complex; and
e. measuring the label free in the reaction mixture or bound on the support of step d to determine the presence of the target antigen.

Finally, the method of performing a competitive immunoassay of this invention comprises the steps of:
a. forming a primary chromatographic support containing a flocculating agent immobilized thereon;
b. forming a secondary support consisting of microparticles containing attached target antigen or its analog;
c. forming a reaction mixture consisting of a sample suspected of containing a target antigen, the microparticles of step b and an antibody to the target antigen coupled to a label;
d. contacting the reaction mixture of step b with the support of step a to trap the microparticles containing the labeled antibody captured thereon; and
e. measuring the label free in the reaction mixture or bound on the support of step d to determine the presence of the target antigen.

DESCRIPTION OF THE INVENTION

The present invention is based on a surprising discovery that a chromatographic support containing flocculating agent immobilized thereon provided a simple, rapid and inexpensive means of separating microparticles. This separation means can be applied to a variety of processes including affinity separation and heterogeneous immunoassays. Major advantages of using the method of the present invention include: conservation of precious reagents, rapid separation, ease of handling, ease of automation and broad applicability to a wide variety of microparticles.

In general, there are two preferred ways to apply the method of the present invention. In the first approach, a chromatographic support containing flocculating immobilized agent can be used to prepare a column to trap microparticles. And, in the second approach, microparticles can be first mixed with a chromatographic support containing immobilized flocculating agent to form the support with the flocculated microparticles, then the resulting support is used to prepare a column.

By microparticles is meant particles in the size range of 0.1 to 10 micrometers, preferably, 1 to 5 micrometers. Such particles are those commonly used in affinity separation and heterogeneous immunoassays. The microparticles may be organic, inorganic, polymeric or a combination thereof.

By chromatographic support is meant any resin commonly used for chromatographic separation. For example, a chromatographic support can be Sephadex G series or Biogel series resins. The chromatographic support may also be a porous plastic. The support may be packed in a column, used in a batch process or provided in the form of a membrane.

Any flocculating agent can be used in the method of this invention, but PEI is preferred. PEI can be attached to suitable supports in a variety of different ways. PEI can be attached to Sephadex type resins by a periodate oxidation method. In this method, the Sephadex is washed and then oxidized with periodate to generate aldehyde functional groups. The PEI is then added and Schiff bases are allowed to form between the aldehyde groups and the amine groups of the PEI. These Schiff bases are then reduced using sodium cyanoborohydride.

The derivatized resin is ready for use after being washed and equilibrated with a suitable buffer.

Another means of attaching PEI to a support is simple adsorption. When a porous plastic rod, such as those available from Porex Technologies (Fairburn, Ga.), is used, this can be accomplished by soaking said rods in a 3% solution of PEI in 30% isopropanol overnight. The rods are then washed with water and an appropriate buffer and are then ready for use. When polyacrylamide resins, such as those available from Bio-Rad under the trade name Biogel, are used, this can be accomplished by soaking the resin in a 3% solution of PEI in 0.1 M sodium chloride. These are only representative procedures and many alternatives will be recognized by anyone skilled-in-the-art. The PEI derivatized supports of Vanecek, et al. and Flasher are also expected to function in this invention. The adsorption approach can also be used to immobilize a flocculating agent on the solid supports. One such example is attachment PRIMAFLOC ® Flocculating reagent (Rohm and Hass, Philadelphia, Pa.) on Sephadex G-10.

In addition to the Sephadex, Biogel and porous plastic type supports discussed above, other types of support can be utilized. The support itself should be nonreactive and exhibit low nonspecific binding of target ligand or binder for the ligand. The porosity of the support can be adjusted to optimize the flow rate for separation of specific microparticles. It is frequently preferred to use column packing material with minimal retention of small molecules such as enzyme substrates. By using such supports, an enzyme bound to a microparticle can be assayed while it is trapped on the column by the action of the flocculating agent. The substrate and product used in said assay can then be readily eluted through the column and detected by spectral means. If these substances were too retarded, this would delay completion of the assay. Then, a support such as Biogel P-2 is preferred.

Buffers suitable for use in this invention are generally those compatible with the biological reagent and samples. Phosphate buffers are generally preferred.

As stated above, one of the great advantages of the method of this invention is the ability to use a wide variety of particles in the method. The preferred particles will, in general, be small and have low nonspecific binding of the target ligand or binder for the ligand. While microparticles are preferred, larger particles can be used; however, the particles should not be so large as to occlude the column. If larger particles are desired it is possible to adjust the porosity of the column packing material to achieve an acceptable flow rate. Inorganic metal oxide or metal silicate particles such as Zinc Orthosilicate:Manganese (Sylvania Chemicals/Metals) can be used. Latex particles of the type disclosed by Craig, et al. (U.S. Pat. No. 4,401,765 issued Aug. 30, 1983) can also be used. Magnetic particles such as those available from Advance Magnetics under the trade name BioMag are also suitable. The preferred particle is, however, the stabilized chromium dioxide particle described in U.S. Pat. No. 4,661,408 issued Apr. 28, 1987, incorporated herein by reference. These particles consist of a core of rutile chromium dioxide which has been extensively surface reduced, coated with alumina, further coated with silica containing borate, and still further coated with a silane to which is attached desired ligand or binder for the ligand. These particles have large surface areas 40 to 100 $m^2/g$ are stable in an aqueous solution and easily coupled to ligand or binder for the ligand.

By ligand is meant an antigen, hapten, nucleic acid, enzyme substrate, vitamin, dye or other smell molecule including enzyme activators and inhibitors; and by binder for the ligand is meant an antibody, enzyme, nucleic acid, binding protein, synthetic mimics of binding proteins such as polylysine or other molecules capable of specific binding interactions. Ligands or binders for the ligands can be readily affixed to particles by a variety of known methods. Covalent attachment is generally preferred to avoid loss of capacity and degradation of performance over time.

Many assay formats are known in the art of heterogeneous immunoassays. This method is applicable to achieving the required separation in any of the known formats. The following discussion is presented to provide a general outline of how this can be accomplished. The skilled artisan will quickly recognize other means to employ the method of this invention.

The method of this invention can be applied to separation of solid support bound and free label in a competitive immunoassay. For example, the bound label is captured onto a microparticle and that particle is trapped by the flocculating agent immobilized on a column. The free label is eluted through the column making it available for detection. If the label is an enzyme, then the bound fraction may be detected instead by eluting a substrate through the column by halting the elution to allow the substrate to react with the enzyme then resuming the elution to elute the product which can then be quantitated.

The method of this invention can be applied to separation in a sandwich immunoassay. In this format, a first capture antibody is affixed to the microparticle. This particle is reacted with a sample containing a target antigen and a second labelled antibody. After allowing suitable time for reaction, the mixture is eluted through a column containing the flocculating agent immobilized thereon to trap the microparticles onto which the labelled antibody is bound by the target antigen which in turn is bound to the capture antibody forming a ternary complex. The unbound or free label in the reaction mixture may be quantitated, but it is frequently advantageous to assay the bound label. As described above, when the label is an enzyme, bound label can be easily determined.

The method of this invention can also be applied to conducting a bioaffinity separation. A bioaffinity column can be prepared by attaching a ligand or binder for the ligand to a microparticle. This particle is then trapped on a column containing the immobilized flocculating agent. This column can then be used as a standard bioaffinity column, that is, mixtures can be passed over it and the target ligand or binder for the ligand can bind to complementary binder for the ligand or ligand. Once the contaminating substances are eluted, the bound ligand or binder for the ligand can then be released by an appropriate elution buffer. One example of how this might be used is protein A coated particles. Protein A binds most subclasses of $I_gG$ immunoglobulins. A flocculating reagent column with protein A particles trapped on it would be useful for removing $I_gG$ immunoglobulins from serum. The $I_gG$ can be recovered by a chaotropic agent.

The method of this invention can also be applied to affinity column mediated immunoassays (ACMIA). A representative ACMIA assay is described by Freytag et al. [Clin. Chem., Volume 30, 417–420 (1984)] for the aca ® discrete clinical analyzer (E. I. du Pont de Nemours and Co., Inc., Wilmington, Del.). An affinity column is prepared as described above, and then used as described by Freytag, et al. It has been found that for a digoxin assay as disclosed by Freytag, et al. the amount of ouabain-BSA required is reduced by over 300 fold using the method of this invention.

It is also recognized that many chemical precipitates form as small particles. These particles can be removed by the method of this invention. Such precipitates can be formed as the result of immunoprecipitation, that is, the formation of large aggregates of antigens and antibodies, or the result of chemical precipitation. One example of chemical precipitation is the use of buffered phosphotungstic reagent to precipitate low density and very low density lipoproteins to allow quantitation of high density lipoproteins. One example of immunoprecipitation is the direct reaction of anti-immunoglobulin antibodies with immunoglobulins as used in the nephelometric or turbidimetric quantitation of immunoglobulins.

Surprisingly, it has been found that columns containing immobilized flocculating agent provide a very simple, efficient means for removing small particles from a liquid suspension. This property makes the use of these columns in bioaffinity separations, and particularly immunoassays, very advantageous.

The following examples further illustrate the invention.

EXAMPLE 1

Trapping of Zinc Orthosilicate:Manganese Particles on Sephadex G-10 Column Containing Flocculating Agent Immobilized Thereon

A. Preparation of PEI-Sephadex G-10 Column

A sample of 16.6 grams of Sephadex G-10 resin (Pharmacia Biotechnology Products) was heated in boiling water for 10 minutes and washed twice each with 100 mL of distilled water. To the swelled resin was added 0.66 g of sodium periodate in 33 mL of distilled water. The mixture was reacted in the dark for two hours at room temperature, washed twice with water and twice with 0.15 M sodium phosphate pH 7.8 buffer. The final suspension was made up with 90 mL phosphate buffer; 60 mL of which was mixed with 2 g of 30% polyethyleneimine (PEI, Cordova Chemical Company) and 10 mg of sodium cyanoborohydride. The pH of the mixture was adjusted to 5.7 with 6 N hydrochloric acid. The mixture was stirred overnight at room temperature and washed 3 times each with 100 mL phosphate buffer. The resin was used in columns designed for use with an automated clinical analyzer (aca ® from E. I. du Pont de Nemours and Co., Inc.). The column is a plastic tube approximately 5.5 mm in diameter and 88 mm long with rubber stoppers at both ends which allow for automatic sample and diluent entry and eluent exit into an analytical test pack. Such an analytical test pack has been described in RE 29795, issued to Johnson, D. R., et al.

B. Preparation of PRIMAFLOC ® flocculating reagent-Sephadex G-10 Column

Fifty grams of Sephadex G-10 were washed twice each with 100 mL of distilled water, and mixed with 1.5 g. PRIMAFLOC ® flocculating reagent (Rohm and Hass, Philadelphia, Pa.) in 150 mL of 0.1 M sodium phosphate buffer (pH 7.0) at room temperature for one hour. The resin was washed with 3×200 mL phosphate buffer and packed into columns as in A.

C. Trapping of Metal Silicate Particles

One hundred $\mu$L of a 10% Zinc Orthosilicate:Manganese particles (Sylvania Chemicals/Metals, Towanda, Pa.) suspension in 0.1 M sodium phosphate buffer (pH 7.0) was injected into each of columns A and B and a similar column packed with unmodified Sephadex G-10 resin. This was followed by eluting each column with 3 mL of the phosphate buffer. Presence of the particles was detected by the green fluorescence of the particles using a short wavelength ultraviolet lamp. Both columns A and B were capable of trapping the particles and particles could only be detected in the top half of the columns. On the other hand, most of the particles passed through the underivatized Sephadex G-10 column into the filtrate.

EXAMPLE 2

A. Preparation of PEI Sephadex G-10 Column

The column was prepared essentially as described in Example 1A.

B. Preparation of Ouabain-BSA-CrO$_2$ Particles

Chromium dioxide magnetic particle containing ouabain/BSA conjugate attached thereon prepared as described in Example 1, U.S. Pat. No.4,661,408.

C. Assay Procedures

To 200 $\mu$L of 0.15 M sodium phosphate buffer (pH 7.8) was added 200 $\mu$L of digoxin antibody-enzyme conjugate reagent (E. I. du Pont de Nemours and Co., Inc., Wilmington, Del.) and 200 $\mu$L of human serum containing digoxin. The digoxin antibody-enzyme conjugate reagent is a covalent conjugate of F(ab')$_2$ antibody fragment from rabbit anti-digoxin antisera and $\beta$-galactosidase. The mixture was incubated at room temperature for ten minutes and 200 $\mu$L of a 10 mg/mL suspension of ouabain-BSA-CrO$_2$ particles were added. Incubation was continued for five more minutes at room temperature. The mixture was transferred to a sample cup for the aca ® analyzer and 400 $\mu$L of it was pipetted by the instrument and injected into the digoxin pack containing a column prepared as above. The particles were trapped by the column and the enzyme activity of the filtrate was measured by the analyzer automatically using-$\beta$-D-galactopyranoside as substrate. A series of human serum samples containing digoxin at concentrations from 0 to 5 ng/mL were tested as described. The 0 ng/mL background (B.G.) and the response difference between 0 and 5 ng/mL (Delta 0,5) were determined and were 18 mA/min and 64 mA/min, respectively.

EXAMPLE 3

Bound Phase Digoxin Assay Using PEI Absorbed on Porous Plastic

A. Preparation of Column

Fifteen $\mu$m pore size porous plastic rods approximately 5.3 mm in diameter and 80 mm long were obtained from Porex Technologies (Fairburn, Ga.). About 20 rods were soaked in a 3% PEI solution in 30% isopropanol with gentle mixing overnight. The columns were rinsed with distilled water and inserted into empty columns described in 1.A. for use on the aca ® analyzer. The column was then washed with 5 mL of 0.15 M sodium phosphate, pH 7.8.

B. Assay Procedures

To a test tube was added 50 μL of digoxin antibody-enzyme conjugate reagent, 50 μL of human serum containing digoxin and 50 μL of 1.15 M sodium phosphate (pH 7.8) and vortexed. The mixture was incubated at 37° C. for ten minutes and 50 μL of a 10 mg/mL suspension of ouabain- BSA-$CrO_2$ particles prepared in 1.B. were added and mixed well. The mixture was incubated for another two minutes and a 150 μL aliquot was injected into a column prepared above and eluted with 2 mL of 0.15 M phosphate. One mL of 0.1M o-nitrophenyl-β-D-galactopyranoside was injected into the column and incubated at 37° C. for ten minutes. The column was then eluted with 2 mL of 0.15 M phosphate and the absorbance at 406 nm was recorded.

C. Results

The B.G. was 307 mA/min and the Delta 0,5 was 200 mA/min. This procedure was repeated using 50 μM pore size porous plastic rods. The B.G. was 268 mA/min and the Delta 0,5 was 162 mA/min.

EXAMPLE 4

TSH Sandwich Assay Using PEI Adsorbed on Biogel P-2

A. Preparation of Column

A sample of 40 g of Biogel P-2 (100–200 mesh) and 10 g of PEI were mixed in 300 mL of 0.1M sodium chloride at room temperature overnight. The resin was washed three times with 300 mL each of 0.1 M sodium chloride and packed into a column for use on the aca ® analyzer as described in 1.A. The column was equilibrated with 80 mm NaCl, 0.1% Tween-20, pH 6.0.

B. Anti-TSH-$CrO_2$ Particle Preparation

I. Reductive Surface Treatment of $CrO_2$

Two hundred and fifty grams of upgraded $CrO_2$ were mixed with 100 g of sodium bisulfite in 1750 mL of water. The mixture was milled in a W-250V-B vertical Belt-Drive Colloid Mill (Greerce Corporation, Hudson, N.H.) for 45 minutes. The particles were washed with water and spray dried. Twenty grams of spray dried $CrO_2$ particles were washed twice with 200 mL of distilled water by decantation. The particles were dispersed in 200 mL of distilled water containing 20 g of sodium bisulfite and 50 g of ⅜" glass beads in a 200 mL tissue culture flask. The mixture was rotated at 5 rpm for 48 hours at room temperature. The particles were separated from the glass beads and washed three times with 200 mL of 10 mM sodium phosphate buffer (pH 7) using magnetic separation.

II. Protein Coupling

Ten mL of a 5% slurry of silanized $CrO_2$ were washed three times with 50 mL each of 10 mM phosphate, pH 7.4. After the third wash, the particles are magnetically separated, the glutaraldehyde was added and rocked for three hours at room temperature. The glutaraldehyde activated particles were washed ten times with 50 mL each of coupling buffer (10 mm potassium phosphate, pH 7.4). After the last wash, the particles were resuspended in 10 mL buffer. To this was added 6 mg of purified α subunit specific antibody in 10 mL of coupling buffer and the mixture rocked for 20 hours at 4° C. The antibody coupled particles were washed once with coupling buffer, then the unreacted aldehyde groups were quenched by reaction with 50 mL of i M glycine, pH 8.0 for ten minutes. The particle reagent was washed extensively, ten times with 50 mL each of the wash buffer (coupling buffer also containing 0.1% BSA), to remove all noncovalently bound antibodies. The final reagent was resuspended into 10 mL of the wash buffer containing 0.1% sodium azide as preservative, and stored at 4° C.

C. Assay Procedures

To a test tube was added 150 μL of human serum containing a known amount of TSH and 25 μL of the antibody conjugate reagent from a Hybritech Tandem ®-e TSH immunoenzymetric assay kit (Hybritech, Inc., San Diego, Calif.) and vortexed. The mixture was incubated at 37° C. for ten minutes and 25 μL of anti-TSH-$CRO_2$ particles (25 mg/mL) was added vortexed. Incubation was continued for another ten minutes and 150 μL of the mixture was injected into a column prepared above. The column was washed with 2 mL of 80 mM sodium chloride and 0.1% Tween-20, pH 6.0 buffer. One mL of 3 mM p-nitrophenylphosphate in 1 M diethanolamine, 0.5 mM $MgCl_2$, pH 8.9 was injected into the column. The column was incubated at 37° C. for 30 minutes and eluted with 2 mL of 50 mM ethylenediamine tetraacetic acid (EDTA), pH 8.9. The absorbance of the eluent at 406 nm Was measured. The 0 μIU/mL background (B.G.) and the response difference between 0 μIU/mL and 50 μIU/mL (Delta 0,50) were determined from those results and were 126 mA/min and 312 mA/min, respectively.

EXAMPLE 5

ACMIA Digoxin Assay Using Ouabain-BSA-$CrO_2$ Particles Trapped on PEI-Biogel P-2 as Affinity Column

A. Preparation of Column

PEI-Biogel P-2 columns were prepared as in Example 3.A. To the column was injected 50 to 200 μL of 10 mg/mL suspensions ouabain-BSA-$CrO_2$ particles. The columns were washed with 3 mL of 0.15 M sodium phosphate buffer (pH 7.8) and inserted into the commercial digoxin pack for the aca ® analyzer (E. I. du Pont de Nemours and Co., Inc.).

B. Assay Procedures

Five hundred μL of human serum containing digoxin and 500 μL of antibody-enzyme conjugate (enough for two tests) were mixed in a sample cup and were incubated at room temperature for ten minutes. Four hundred μL of the mixture were pipetted by the aca ® analyzer and processed as the commercial method.

The test results using different amounts of particles trapped on the column are compared to the commercial method which uses ouabain-BSA-Sephadex G-10 in Table 1:

TABLE 1

| Digoxin Assay Using Trapped $CrO_2$ Particles on aca ® | | |
|---|---|---|
| Particles mg | Background (mA/min) | Separation Delta, 0, 5 (mA/min) |
| 0.5 | 88 | 68 |
| 1.0 | 60 | 91 |
| 2.0 | 48 | 84 |

TABLE 1-continued

Digoxin Assay Using Trapped CrO₂ Particles on aca ®

| Particles mg | Background (mA/min) | Separation Delta, 0, 5 (mA/min) |
|---|---|---|
| Commercial Pack | 72 | 79 |

EXAMPLE 6

Affinity Purification of Anti-Digoxin Antibody

PEI-Biogel P-2 resin was prepared as in Example 3.A. and packed in a 1.5×15 cm column. The column was washed with 100 mL of 10 mM sodium phosphate (pH 7.0) containing 0.9% of sodium chloride (PBS). Three mL of a 50 mg/ml suspensions ouabain-BSA-$CrO_2$ particles prepared in Example 1.B. were loaded on the column. The top of the column was intentionally disturbed to mix the top half of the resin with the $CrO_2$ particles and allowed to pack again. The packed column was washed with mL of PBS, no leakage of the $CrO_2$ particles was observed. Ten mL of rabbit anti-digoxin serum were loaded on the column and the serum was allowed to incubate for 15 minutes. The unbound fraction was eluted with 100 mL of PBS. The bound anti-digoxin was eluted with 2.5 M ammonium thiocyanate (pH 7.8). Fractions containing the protein were identified by monitoring the 280 nm absorbance and were pooled and dialyzed against PBS. Immunodiffusion analysis indicated that all the anti-digoxin was in the bound fractions, no anti-digoxin was observed in the unbound fractions.

EXAMPLE 7

Automated Assay for High Density Lipoprotein (HDL) Cholesterol

The following procedures can be used to perform an assay for high density lipoprotein (HDL) cholesterol which automated the removal of the low density and very low density lipoprotein which are precipitated when the sample is pretreated with phosphotungstic acid.

A. Preparation of Column

PEI-Biogel P-2 columns for the aca ® analyzer are prepared as described in Example 3.A. These columns are then placed in the header of an analytical test pack (as described in Example 1.A.) which contains the reagents necessary to assay for HDL cholesterol.

B. Assay Procedure

Five hundred μL of serum and 100 μL of a 20 g/L solution of phosphotungstic acid are mixed in an aca ® analyzer sample cup and allowed to stand for five minutes. Two hundred and fifty μL of this pretreated sample are then injected into the column described [from] 6.A. The column is eluted with 4.75 mL of 10 mM sodium phosphate buffer (pH 7.0). The filtrate is collected in the analytical test pack which can be processed on an aca ® analyzer to determine the quantity of HDL cholesterol present.

What is claimed is:

1. A method of performing an affinity separation comprising the steps of;
   a. forming a primary chromatographic support with a flocculating agent immobilized thereon, the primary support selected from the group consisting of particulate resins and porous plastic materials;
   b. forming a secondary support consisting of microparticles having ligand or binder for the ligand affixed thereon;
   c. contacting the primary support of step a with the secondary support of step b to form an affinity support with said microparticles flocculated onto said primary support; and
   d. contacting a sample suspected of containing a binder or ligand complementary to the ligand or binder attached on the affinity support of step c to separate said binder or ligand from the sample.

2. The method of claim 1 wherein the flocculating agent is polyethyleneimine.

3. The method of claim 2 wherein the primary support is a particulate resin packed in a column.

4. The method of claim 3 wherein the microparticles are chromium dioxide magnetic particles.

5. A method of performing affinity separation comprising the steps of:
   a. forming a primary chromatographic support with a flocculating agent immobilized thereon, the primary support selected from the group consisting of particulate resins and porous plastic materials;
   b. forming a secondary support consisting of microparticles having ligand or binder for the ligand affixed thereon;
   c. contacting a sample suspected of containing a binder or ligand complementary to the ligand or binder attached on the microparticles of step b with said microparticles to capture the binder or ligand from the sample onto the microparticles; and
   d. contacting the reaction mixture of step c with the primary support of step a to trap the microparticles.

6. The method of claim 5 wherein the flocculating agent is polyethyleneimine.

7. The method of claim 6 wherein the primary support is a particulate resin packed in a column.

8. The method of claim 7 wherein the microparticles are chromium dioxide magnetic particles.

* * * * *